(12) United States Patent
Singhal et al.

(10) Patent No.: US 12,653,534 B2
(45) Date of Patent: Jun. 16, 2026

(54) LYMPHATIC ANASTOMOSIS DEVICES AND METHODS

(71) Applicant: Beth Israel Deaconess Medical Center, Inc., Boston, MA (US)

(72) Inventors: Dhruv Singhal, Chestnut Hill, MA (US); Kieran Singhal, Longview, TX (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 821 days.

(21) Appl. No.: 17/132,946

(22) Filed: Dec. 23, 2020

(65) Prior Publication Data

US 2021/0137523 A1     May 13, 2021

Related U.S. Application Data

(63) Continuation-in-part of application No. PCT/US2020/038806, filed on Jun. 19, 2020.

(Continued)

(51) Int. Cl.

| | |
|---|---|
| *A61B 17/11* | (2006.01) |
| *A61B 34/10* | (2016.01) |
| *A61B 34/20* | (2016.01) |
| *A61B 34/30* | (2016.01) |
| *A61B 90/00* | (2016.01) |

(52) U.S. Cl.
CPC .............. *A61B 17/11* (2013.01); *A61B 34/20* (2016.02); *A61B 34/30* (2016.02); *A61B 90/39* (2016.02); *A61B 2017/1107* (2013.01); *A61B 2017/1132* (2013.01); *A61B 2034/107*

(2016.02); *A61B 2034/108* (2016.02); *A61B 2090/3966* (2016.02); *A61B 2090/3983* (2016.02)

(58) Field of Classification Search
None
See application file for complete search history.

(56) References Cited

U.S. PATENT DOCUMENTS

| | | |
|---|---|---|
| 3,316,914 A | 5/1967 | Collito |
| 4,523,592 A | 6/1985 | Daniel |

(Continued)

FOREIGN PATENT DOCUMENTS

| | | |
|---|---|---|
| CN | 107088079 A | 8/2017 |
| CN | 307035339 | 12/2021 |

(Continued)

OTHER PUBLICATIONS

Spiguel et al., "Fluorescein Isothiocyanate: a Novel Application for Lymphatic Surgery", Ann Plast Surg. Jun. 2017;78(6S Suppl 5): S296-S298. pre-publication edition. (Year: 2017).*

(Continued)

*Primary Examiner* — Elizabeth Houston
*Assistant Examiner* — Lindsey Bachman
(74) *Attorney, Agent, or Firm* — McCarter & English, LLP

(57) ABSTRACT

Preferred embodiments relate to devices and methods for performing a lymphovenous bypass procedure. A first ring is secured to tissue connected to at least one lymphatic channel of a patient and a second ring is attached to a vein of the patient. An end of the lymphatic channel that extends through the first ring is inserted into an open end of the vein and the rings are connected together to establish fluid flow from the lymphatic channel into the vein.

26 Claims, 10 Drawing Sheets

Related U.S. Application Data

(60) Provisional application No. 62/864,862, filed on Jun. 21, 2019.

(56) References Cited

U.S. PATENT DOCUMENTS

| | | | |
|---|---|---|---|
| 5,855,583 | A | 1/1999 | Wang et al. |
| 6,030,395 | A | 2/2000 | Nash et al. |
| 6,569,173 | B1 | 5/2003 | Blatter et al. |
| 6,575,985 | B2 | 6/2003 | Knight et al. |
| 6,736,824 | B2 | 5/2004 | Borghi |
| D536,068 | S | 1/2007 | Grether |
| 7,182,771 | B1 | 2/2007 | Houser et al. |
| 7,192,400 | B2 | 3/2007 | Campbell et al. |
| 7,526,337 | B2 | 4/2009 | Shuros et al. |
| D616,090 | S | 5/2010 | Kawamura |
| D622,356 | S | 8/2010 | Grether et al. |
| 8,109,949 | B2 | 2/2012 | Blatter et al. |
| 8,313,013 | B2 | 11/2012 | Kuester, III et al. |
| D674,088 | S | 1/2013 | Lev et al. |
| 8,367,124 | B2 | 2/2013 | Kajiya et al. |
| 8,905,999 | B2 | 12/2014 | Shuros et al. |
| 9,138,297 | B2 | 9/2015 | Brisson et al. |
| 9,421,316 | B2 | 8/2016 | Leeflang et al. |
| D775,342 | S | 12/2016 | LeBlanc et al. |
| 9,642,623 | B2 | 5/2017 | Agarwal et al. |
| D817,760 | S | 5/2018 | Petrosino et al. |
| D901,005 | S | 11/2020 | Guala |
| 2003/0088255 | A1 | 5/2003 | Borghi |
| 2004/0129347 | A1 | 7/2004 | Craig |
| 2004/0249335 | A1 | 12/2004 | Faul et al. |
| 2005/0149075 | A1 | 7/2005 | Borghi et al. |
| 2005/0216043 | A1 | 9/2005 | Blatter et al. |
| 2006/0058844 | A1 | 3/2006 | White et al. |
| 2007/0250082 | A1 | 10/2007 | Kansoul |
| 2010/0036397 | A1* | 2/2010 | Kang ..................... A61B 17/11 |
| | | | 606/153 |
| 2010/0114293 | A1 | 5/2010 | Heaton, II et al. |
| 2010/0174300 | A1 | 7/2010 | Blondeel |
| 2014/0052160 | A1* | 2/2014 | Singh ..................... A61B 17/11 |
| | | | 606/153 |
| 2016/0206316 | A1 | 7/2016 | Johnson et al. |
| 2016/0278780 | A1* | 9/2016 | Ishii ....................... A61B 17/11 |
| 2016/0289763 | A1 | 10/2016 | Muthuchamy et al. |
| 2016/0324522 | A1 | 11/2016 | Agarwal et al. |
| 2017/0258965 | A1 | 9/2017 | Reichmann et al. |
| 2018/0214201 | A1 | 8/2018 | Bargon et al. |
| 2018/0256139 | A1 | 9/2018 | Miller et al. |
| 2019/0038288 | A1 | 2/2019 | Rosello |
| 2019/0099185 | A1 | 4/2019 | Kahana et al. |
| 2019/0125349 | A1* | 5/2019 | Kahana ................... A61F 2/064 |
| 2019/0380712 | A1 | 12/2019 | Florescu |
| 2020/0138708 | A1 | 5/2020 | Labib et al. |
| 2022/0192668 | A1 | 6/2022 | Singhal et al. |
| 2022/0354499 | A1 | 11/2022 | Singhal et al. |
| 2024/0415513 | A1 | 12/2024 | Singhal |

FOREIGN PATENT DOCUMENTS

| | | |
|---|---|---|
| DE | 102008055587 A1 | 8/2009 |
| DE | 102009048433 A1 | 4/2011 |
| JP | 46-3697 B2 | 11/1971 |
| JP | D1716622 | 6/2022 |
| KR | 10-1126220 B1 | 3/2012 |
| TW | 201114457 A | 5/2011 |
| TW | 201238618 A | 10/2012 |
| TW | 201410287 A | 3/2014 |
| WO | 2017/040884 A1 | 3/2017 |
| WO | 2017/158602 A1 | 9/2017 |
| WO | 2020/225603 A1 | 11/2020 |
| WO | 2020/257700 A2 | 12/2020 |
| WO | 2022/010601 A1 | 1/2022 |

OTHER PUBLICATIONS

Pond et al., "Interactions between adipose tissue around lymph nodes and lymphoid cells in vitro", Journal of Lipid Research vol. 36, 1995, pp. 2219-2231. (Year: 1995).*

Chang et al., "Lymphovenous Anastomosis Bypass Surgery", Semin Plast Surg 2018;32:22-27. (Year: 2018).*

Chen et al., Immediate Limb Compression Following Supermicrosurgical Lymphaticovenular Anastomosis—Is It Helpful or Harmful? International Microsurgery Journal. 2018;2(1):1 (Year: 2018).*

Kung et al., Current Concepts in the Surgical Management of Lymphedema Plastic and Reconstructive Surgery 139(4):p. 1003e-1013e, Apr. 2017. (Year: 2017).*

Hahamoff et al., Lymphedema Surveillance Program for Breast Cancer Patients Reveals the Promise of Surgical Prevention. J Surg Res. Dec. 2019;244:604-611. pre-publication edition.

Johnson et al., Lymphedema Incidence After Axillary Lymph Node Dissection: Quantifying the Impact of Radiation and the Lymphatic Microsurgical Preventive Healing Approach. Ann Plast Surg. Apr. 2019;82(4S Suppl 3):S234-S241.

Margaris et al., Modelling the lymphatic system: challenges and opportunities. J R Soc Interface. Apr. 7, 2012;9(69):601-12.

Munn et al., Imaging the lymphatic system. Microvasc Res. Nov. 2014;96:55-63.

Nuri et al., End-to-End Lymphaticovenular Anastomosis Does Not Disturb the Contraction of Collecting Lymph Vessels. Plast Reconstr Surg Glob Open. Sep. 5, 2017;5(9):e1457, 2 pages.

Spiguel et al., Fluorescein Isothiocyanate: a Novel Application for Lymphatic Surgery. Ann Plast Surg. Jun. 2017;78 (6S Suppl 5):S296-S298. pre-publication edition.

Van Mulken et al., First-in-human robotic supermicrosurgery using a dedicated microsurgical robot for treating breast cancer-related lymphedema: a randomized pilot trial. Nat Commun. Feb. 11, 2020;11(1):757, 7 pages.

Winters et al., The efficacy of lymphaticovenular anastomosis in breast cancer-related lymphedema. Breast Cancer Res Treat. Sep. 2017;165(2):321-327.

Invitation to Pay Additional Fees for Application No. PCT/US2020/038806, dated Oct. 9, 2020, 17 pages.

International Search Report and Written Opinion for Application No. PCT/US2020/038806, dated Jan. 25, 2021, 29 pages.

International Search Report and Written Opinion for Application No. PCT/US2021/065126, dated Apr. 8, 2022, 17 pages.

An et al., Biocompatibility and patency of a novel titanium vascular anastomotic device in a pig jugular vein. Scientific Reports. 2021;17512, 4 pages.

Dumanian et al., Northwestern and Other Historical Vignettes regarding the Vascular Anastomotic Coupling Device. Plast Reconstr Surg Glob Open. 2019;7:e2194, 6 pages.

NIH, Components of the Lymphatic System. SEER Training Modules. 2 pages. Accessed Nov. 6, 2024.

ResearchGate, retrieved online at: <https://www.researchgate.net/figure/Diagram-of-vascular-anastomotic-coupler-of-Holt-23-image-courtesy-by-the-archives-of-the_fig3_333218572.> 1 page, May 2019.

International Search Report and Written Opinion for Application No. PCT/US2024/035288, dated Aug. 26, 2024, 17 pages.

* cited by examiner

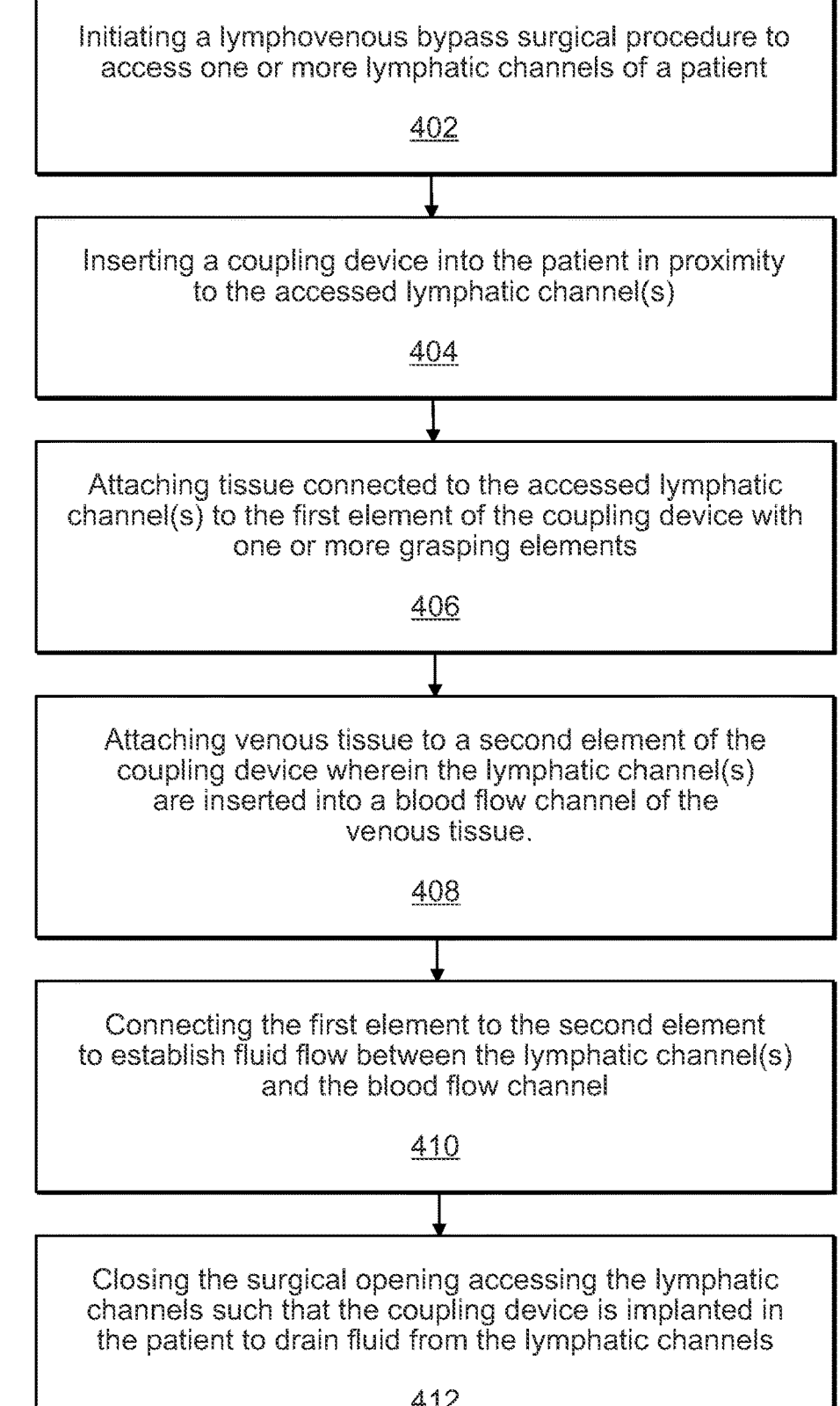

400

Initiating a lymphovenous bypass surgical procedure to access one or more lymphatic channels of a patient

402

Inserting a coupling device into the patient in proximity to the accessed lymphatic channel(s)

404

Attaching tissue connected to the accessed lymphatic channel(s) to the first element of the coupling device with one or more grasping elements

406

Attaching venous tissue to a second element of the coupling device wherein the lymphatic channel(s) are inserted into a blood flow channel of the venous tissue.

408

Connecting the first element to the second element to establish fluid flow between the lymphatic channel(s) and the blood flow channel

410

Closing the surgical opening accessing the lymphatic channels such that the coupling device is implanted in the patient to drain fluid from the lymphatic channels

Figure 8:
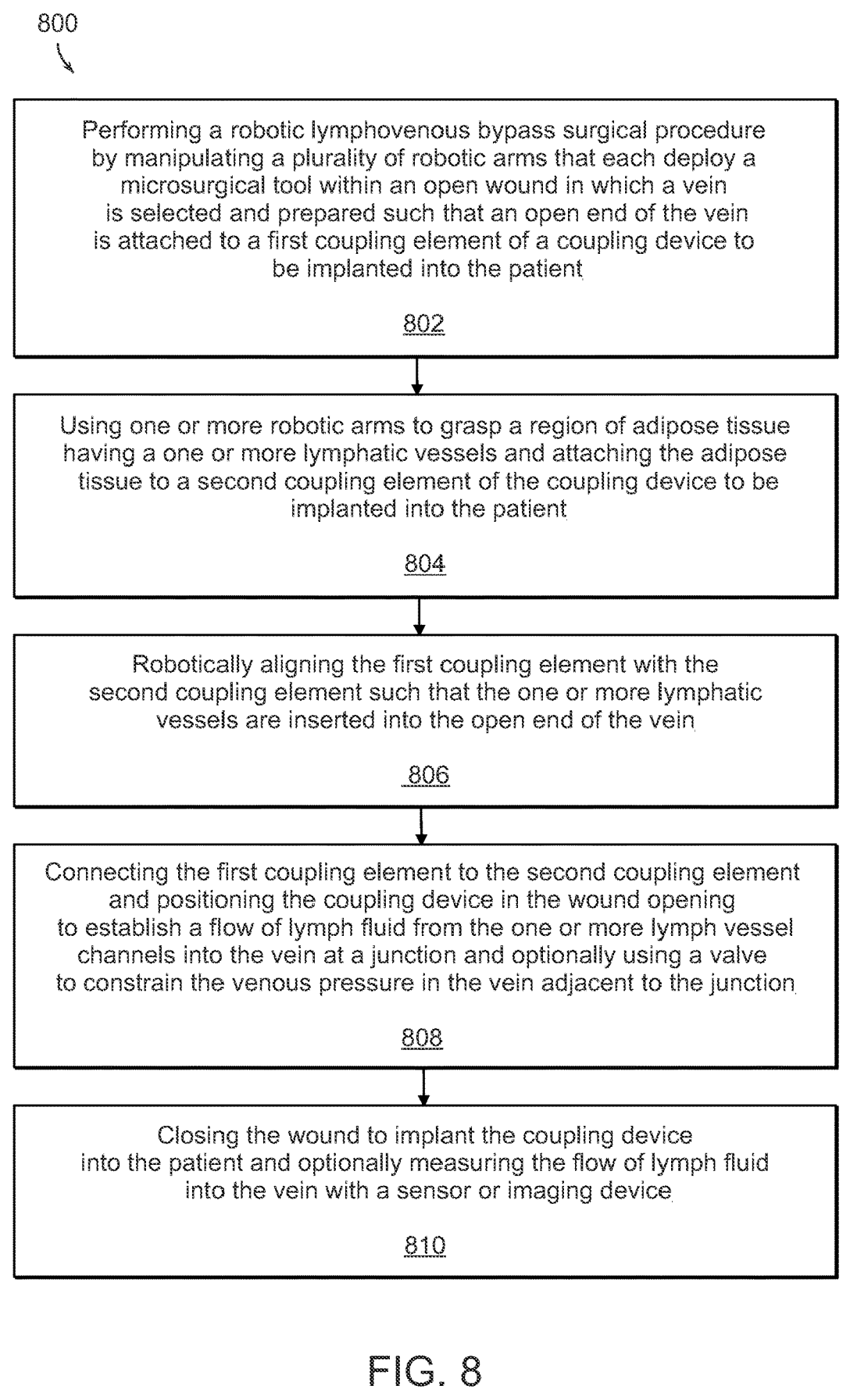

Performing a robotic lymphovenous bypass surgical procedure
by manipulating a plurality of robotic arms that each deploy a
microsurgical tool within an open wound in which a vein
is selected and prepared such that an open end of the vein
is attached to a first coupling element of a coupling device to
be implanted into the patient

802

Using one or more robotic arms to grasp a region of adipose tissue
having a one or more lymphatic vessels and attaching the adipose
tissue to a second coupling element of the coupling device to be
implanted into the patient

804

Robotically aligning the first coupling element with the
second coupling element such that the one or more lymphatic
vessels are inserted into the open end of the vein

806

Connecting the first coupling element to the second coupling element
and positioning the coupling device in the wound opening
to establish a flow of lymph fluid from the one or more lymph vessel
channels into the vein at a junction and optionally using a valve
to constrain the venous pressure in the vein adjacent to the junction

808

Closing the wound to implant the coupling device
into the patient and optionally measuring the flow of lymph fluid
into the vein with a sensor or imaging device

LYMPHATIC ANASTOMOSIS DEVICES AND METHODS

CROSS REFERENCE TO RELATED APPLICATIONS

This application is a continuation-in-part of International Application No. PCT/US2020/038806, filed Jun. 19, 2020, which claims priority to U.S. Provisional Application No. 62/864,862, filed Jun. 21, 2019, the entire contents of each of the above applications is incorporated by reference herein in its entirety.

BACKGROUND

The lymphatic system is a complex system of cellular tissue, vessels and organs that operates to carry excess fluids to the bloodstream and provides important functions to a body's immune system by removing pathogens from the circulatory system. The system includes small organs, or lymph nodes, that number around 500-600 in the human body. Lymphatic capillaries and vessels transport interstitial fluid typically through lymphatic ducts into the circulatory system. Interstitial fluid in the lymphatic system ("lymph") can build up due to disease or injury. An excessive accumulation of this fluid is known as lymphedema.

Breast cancer-related lymphedema (BCRL) is one of the most significant survivorship issues in breast cancer management. Presently there is no cure for BCRL. Of 2.8 million breast cancer survivors in the United States, it is estimated that 1 in 5 suffers from BCRL. Patients presenting with BCRL often complain of tightness, heaviness, fatigue, and inability to fit into clothing secondary to swelling that is commonly experienced with this condition. In select cases, patients present with repeated episodes of rapidly spreading cellulitis of the affected extremity that can be life threatening if not treated expeditiously. The signs and symptoms of BCRL have been associated with a predilection towards anxiety, depression, and overall reduced quality of life. The most common risk factors for the development of BCRL are an axillary lymph node dissection, regional lymph node radiation (RLNR), and/or an elevated BMI (>30).

The standard treatment for BCRL has been physical therapy with manual lymphatic drainage, compression, local skin care, exercises, and pneumatic devices. Surgical management of chronic lymphedema can include lymphovenous bypass and lymph node transfer, however, these do not provide a definitive cure. The single greatest risk factor for developing BCRL is an axillary lymph node dissection (ALND). Lymphatic Microsurgical Preventative Healing Approach (LYMPHA) is a surgical procedure to reduce the risk of lymphedema in patients undergoing an ALND. LYMPHA has been used in patients undergoing ALND who developed lymphedema.

Note that a significant risk factor for the development for lymphedema is an ALND. In one study, 1 of 67 patients undergoing a sentinel lymph node biopsy developed lymphedema (1.5%). On the other hand, 4 of 10 patients who underwent an ALND alone developed lymphedema (40%). However, when LYMPHA was performed at the time of ALND, only 1 of 8 patients developed lymphedema (12.5%). Offering LYMPHA with ALND decreased the institutional rate of lymphedema from 40% to 12.5% in this study for example.

In the LYMPHA procedure, lymphatics draining the arm are identified and bypassed into an axillary vein tributary at the time of an axillary dissection. This technique has demonstrated a 5% lymphedema rate after axillary lymph node dissection (ALND) and LYMPHA over a four year period, for example. Historical rates of lymphedema after ALND are highly variable however, often indicated to be between 20-40% and have been reported as high as 77%.

One challenge of the LYMPHA procedure is visualizing healthy cut lymphatics lateral to the level 1 lymph nodes after an ALND. A technique for identifying these lymphatics can use an injection of blue dye into the ipsilateral proximal upper arm to visualize location. Although most LYMPHA procedures have been performed in the axillary bed, note that other lymph node dissection locations including the neck, chest, abdomen and groin carry a risk of lymphedema development and a bypass can reduce the risk of lymphedema development at these sites and associated extremities. Notwithstanding the improvements in the treatment of lymphedema with the above referenced procedures, further improvements are needed in this procedure to improve the treatment of this condition.

SUMMARY

The present invention relates to a device for coupling one or more lymphatic channels to the vascular system. Of significant note, all other previously described lymphatic and vascular anastomotic devices require vessels of similar caliber to be connected in an end-to-end manner or an end to side manner for a size discrepancy. Preferred embodiments as described herein enable the intussusception of one or more lymphatic channels of significantly different size into a single vein, for example. Consequently, these preferred embodiments of coupling devices facilitate the LYMPHA procedure by improving the speed of the procedure, improving the stability of the resulting anastomosis, and can serve to couple a single lymphatic channel, or plurality of lymphatic channels, into a single vascular channel such as a vein or artery.

The procedure can utilize the fat tissue associated with grouping of one, two or more lymphatic channels to assist in connecting the lymphatic channels to a first coupling element of the device. Prior to beginning the procedure, the lymphatic system in a region of interest can be evaluated by visualization techniques. Dyes may be injected for microscopic imaging and lymphatic mapping to identify a specific region of interest that would serve to drain fluid from an affected region such as an arm of a patient. The surgeon begins the procedure by accessing the site by incision to expose lymphatic channels and one or more veins that can be used, and identifying one of more lymphatic channels to be coupled into a selected vein. Visualization of the implanted device can be improved with fluoroscopic markers attached to, or imbedded within, or positioned on one or more regions of the device. Visualization of lymph flow after implantation of the connector to couple the lymph channels into the vein, or coupling to one or more tributaries of the vein, can be used to monitor the viability of the lymph flow after closure of the surgical wound.

A specific coupling device may be selected based on the number and size of the lymphatic channels and the vein to which they are to be positioned. The device can be fabricated by standard molding and assembly techniques using biocompatible materials such as synthetic polymers or silicone, for example. These may have different sizes and shapes depending on the particular site for implantation. A vein can be attached to a second coupling element that can include an aperture or opening from 1.0 mm to 3.0 mm in diameter, for example. The first and second coupling elements can be shaped as rings with the lymphatic channels connected to extend through the central opening of the first ring and a vein connected to the second ring, the first ring being attached to the second ring such that one or more lymphatic channels extend into the single vein, i.e. the lymphatic channels are intussuscepted into the vein.

In a further embodiment, a connector device can be used to align and connect the first ring to the second ring. The connector device can include one or more cone shaped elements, for example, with a connector channel through which the lymphatic channels can extend through the second ring opening into the vein, that is, the lymphatic channels are intussuscepted, or telescoped into the vein. The cone shaped element(s) can include a shaped surface or surfaces that extend from a larger diameter portion to a smaller diameter portion that extends around the opening of a cavity through which the lymphatic vessels slide into the vein. The cavity can comprise a tubular channel through which the vein is inserted with the wall of the vein being engaged by pins or tissue anchors. The lymphatic vessels and capillaries are embedded within supporting tissue that generally surrounds the vessels. Note that when a lymph node has been removed to address a patient's medical condition, the lymphatic vessels that were connected to that lymph node have been cut and will typically continue to pass lymph fluid that will flow through the cut ends and into the surrounding tissue. The surgeon can expose the ends of the lymphatic vessels that have been cut wherein the ends extend a distance from that portion of the supporting tissue that is attached to the pins or tissue anchors that are sized and shaped to grasp the supporting tissue. The supporting tissue can comprise a fibrous connective tissue that can be manually grasped by the surgeon using forceps or tweezers, for example. These can include grasping instruments having a small tip size to grasp the lymphatic vessels that can have a diameter in a range of 0.1 mm to 1.0 mm, or larger, that are positioned within, or in proximity to, an exposed end of a vein into which the lymph fluid is to be delivered. There are frequently three or four lymphatic vessels in a region about a removed lymph node that can be grasped using the surrounding adipose tissue that supports these lymphatic vessels. The lymphatic vessels are spaced apart, with the surgeon frequently selecting a group of lymphatic vessels for the anastomosis that are spaced sufficiently close that they will fit into the diameter of the vein. Lymph nodes can vary in size depending on the age and medical condition of the patient, but will frequently have a size in a range of 4 mm to 2 cm along the long axis of the lymph node. The size of the present device can vary depending on the size of the vein to be attached to the device, but can also be in a range of 4 mm to 2 cm in diameter. By mounting the supporting tissue onto pins or anchors, this mounting movement tends to cause the cut ends of the lymphatic vessels to extend further from the surrounding tissue and thereby be readily placed into the exposed end of a vein where the end of the vein is mounted onto the pins or anchors. The open end of the vein can be slightly enlarged. The lymphatic vessels can have varying lengths extending from the supporting tissue and thus may be placed into the vein at different insertion lengths or there may be ends of lymphatic vessels that reside outside the end of the vein that nevertheless continue to deliver lymph fluid into the vein. Some of the lymphatic vessels will have higher flow rates so that even those residing outside of the vein after implant of the device and closer of the surgical wound will have sufficient proximity to the vein to preserve flow. A tissue flow channel may form that extends from the end of a high flow lymphatic vessel into the vein.

The first coupling element can have tissue grasping elements such as pins, prongs or tissue anchors that grasp the fatty tissue surrounding the lymphatic channels. Thus, the lymphatic channels extend within channel supporting tissue that can be attached to the first coupling element without impairing lymphatic channel function thereby enabling transport of lymph into the vein such that swelling is reduced. The pins, posts, prongs or tissue anchors can extend through the fatty tissue to engage receiving features on the second coupling element. For embodiments utilizing a connector element between a first ring and a second ring, for example, the pins, prongs or tissue anchors may engage the tissue, and may also engage the connector element.

Surgical tools can be used to grasp the tissue to position it relative to the pins, prongs or tissue anchors to thereby attach the tissue to the anastomosis device. A clamping device can be used to temporarily hold the coupling elements of the device in position to facilitate the attachment of tissue to each element, alignment of the coupling elements and connecting the components together, as needed.

Medical personnel can perform procedures as described herein by first evaluating a patient's condition in which swelling has occurred, or is likely to occur. Visualization techniques as described herein can be used to map those regions of the lymphatic system to select one or more regions thereof that will reduce or eliminate swelling by implantation of one or more devices as described herein. As preferably at least 2, 3, 4, 5 or more lymphatic channels can be fluidly coupled into a single vein, a significant amount of lymph can be removed into a single vein using a single device. After mapping and selection, one or more devices are implanted as described herein.

Further embodiments employ a device in which the lymphatic channels are grasped individually or collectively and placed within the vein at a selected depth. This can be performed manually or by using a robotic device. For example, forceps and/or a loop of suture material can be used to grasp one or more channels and used to place them into the vein attached to the tube or ring. The suture material can be temporarily attached to the tube before biodegrading after closure of the wound over a time period in which the channel tissue and vein tissue heal so as to permanently connect the channels to the vein. A biocompatible adhesive can also be used to attach tissues to the tube, for example. The tube can have surface elements or grooves allowing it to be held by the surgeon for attachment of the vein inserted on one side and connected to pins or prongs as described herein and the channels inserted into the vein at the opposite end of the tube. For robotic surgery, a plurality of controlled arms with manipulating elements can be used isolate and grasp the vein and attach the exposed end to the first coupling element. The controlled arms can also operate to attach the tissue, such as visceral adipose tissue containing the lymphatic vessels, to the second coupling element as described herein. The robotic arms can then be controlled by the surgeon to grasp the first and second elements, bring them into alignment and attached them together as to fluidly couple the lymphatic channels into the vein. The device can then be positioned within the wound opening and the wound sutured so as to close the wound.

In further embodiments, the one or more lymphatic vessels can be fluidly coupled to a vein by attaching the vein and the vessels to a single unitary coupling element. The unitary coupling element can comprise a generally cylindrical body wherein the vein is coupled to a first end of the cylindrical body and the lymphatic vessels to a second end of the cylindrical. Embodiments can further include a more rounded or oval shape. The exterior surface can have slots or grooves that enable a user to more readily grasp the implant device manually or with grasping surgical instruments such as forceps or tweezers. The unitary coupling element will have a first opening to receive the vein at the first end with a first group of pins or anchors positioned around the inside portion of the first opening to secure the open end of the vein within the implant. The second end can have a wider opening than the vein insertion opening to provide for the insertion of the supporting tissue which typically has a larger diameter than the vein as it must incorporate all the spaced apart lymphatic vessels to be inserted into the vein. The sidewall of the implant device that extends around the periphery of the second opening can have sidewall openings or windows through which the surgeon can insert a surgical grasping tool such as forceps, for example, that grasp different regions of the supporting tissue for placement onto the a second group of pins or anchors that generally extend in an opposite direction from the first group of pins or anchors that secure the open end of the vein. The pins or anchors can extend along the longitudinal axis of the implant device, or they can extend radially or at some angle to the longitudinal axis between 1 and 45 degrees, for example, so as provide a more secure attachment.

BRIEF DESCRIPTION OF THE DRAWINGS

FIG. 4 schematically illustrates the steps of a surgical procedure to perform a bypass surgical procedure in accordance with embodiments of the invention.

FIG. 8 illustrates a process flow diagram for performing a robotically controlled surgical process in accordance with preferred embodiments.

DETAILED DESCRIPTION OF THE DRAWINGS

Figure 1:
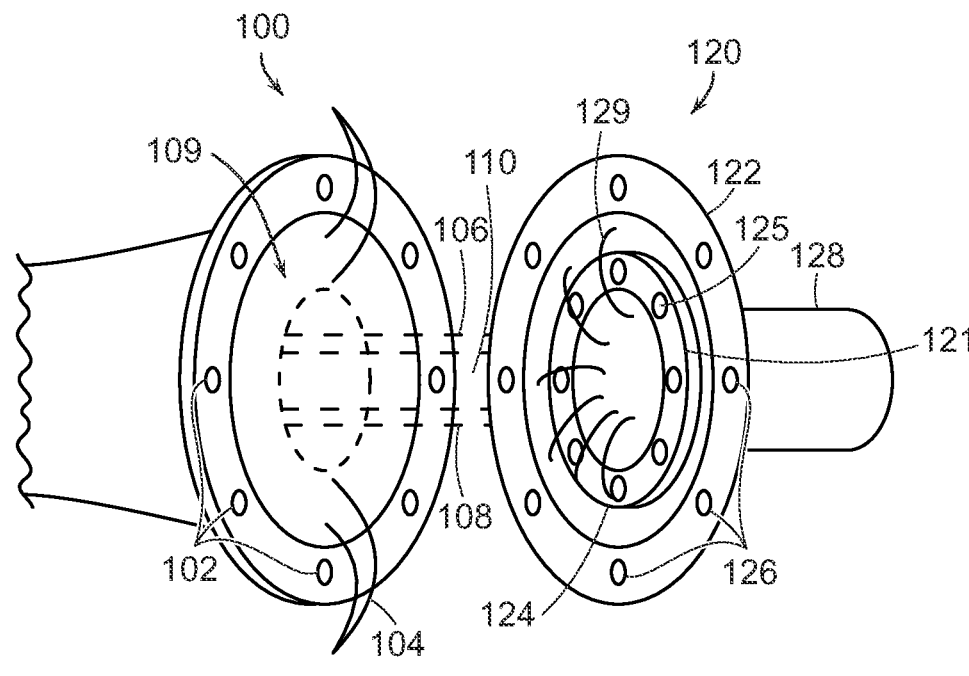
FIG. 1 illustrates an embodiment of a coupling device using a pair of rings to align and connect lymphatic channels to a vein or artery.

Preferred embodiments of the invention utilize a device for coupling one or more lymphatic channels to the vein of a patient's circulatory system. Shown in FIG. 1 is an embodiment of a coupling device in which a first coupling element 100 comprises a ring with a central opening 109 through which the fatty tissue 104 surrounding the lymphatic channels 106, 108 is drawn over pins, prongs or tissue anchors 102 that face inwards from the inner ring surface towards second coupling element 120. Unlike vascular anastomeric couplers used to connect the ends of two blood vessels, the present invention enables the insertion of one or more lymphatic channels into (i.e., an intussusception) an open end of a blood vessel or vein as there is typically a mismatch in size, one lymphatic channel being substantially smaller than the size of the vein into which it is inserted. Thus, one, two or more lymphatic vessels with channels for flow of lymph fluid can be inserted into a single vein 128, depending on the sizes thereof. Note that blood vessels cannot be inserted into one another as clotting can result in anastomosis failure. Lymph fluid, on the other hand, does not clot. The insertion of lymphatic channel tissue into a blood vessel does not induce such clotting and allows flow of lymph into the vessel without obstruction.

The components in FIG. 1 can comprise a rigid or semi-rigid compliant, elastic biocompatible material with generally smooth surface features except for the pins, prongs or tissue anchors that are configured to penetrate and grasp tissue. In selected embodiments, the components provide a sutureless tissue connector, however sutures can be used to augment implantation of the device in some embodiments.

Components of the device can be made using biocompatible materials such as silicone, polyurethane, polytetrafluoroethylene (PTFE), polyesther, polyethylene, polyamide, polyetheretherketone (PEEK), polypropylene, Mylar, Kevlar, polyisoprene, polyolefin, or combinations thereof.

The first coupling element can comprise a ring having a larger opening to accommodate a thickness of fatty tissue, such as visceral adipose tissue (containing lymphatic vessels with channels extending through the vessels to transport lymph fluid), to extend therethrough and surround the lymphatic tissue, which consequently does not contact the connector surfaces. Note that ring elements can have other shapes, such as an oval cross-section, or some other shape suitable for a specific anatomical placement in the patient. The outer surface is preferably smooth to avoid abrading adjacent tissue. Lymphatic vessels are thin walled tubular shaped tissue structures that are lined with endothelial cells and comprise smooth muscle that is connected to surrounding tissue with adventitia. Lymphatic capillaries are smaller, without the muscle and adventitia, and range in diameter from 15-75 microns. The larger lymphatic vessels have valves spaced along their length with fluid movement provided by peristalsis to move lymph fluid through the vessel under fluid pressure. Lymphatic collecting vessels have a diameter in a range of 100-800 microns or larger. A vein of the vascular system can have a diameter of 1 mm or more and can be selected to receive two or more lymphatic channels for each vein selected. Generally a vein will have a diameter in the range of 2-4 mm that will coupled to lymphatic vessels with supporting tissue that fits within a device aperture that is larger than the diameter of the aperture holding the vein. The coupling elements can have a diameter in a range of 1-15 mm and can have matching diameters in embodiments including two coupling elements. The present devices and methods can also be used to couple to one or more smaller tributary veins that feed into a larger vein. The inner surface of the central opening in an inner ring can be large enough to allow passage of the vein through the central opening such that the exposed end of the vein can be attached to the second connector. Thus, the second connector 120 can have the inner ring 124, with pins, prongs, or tissue anchors 125 that engage the tissue of the vein 129 that folds over the pins 125. The outer ring 122 has pin receiving regions 126 that receive and engage the ends of pins 102, for example, that protrude above the ring surface at an elevation sufficient to at least engage the tissue. Region 126 can be configured to snap together with at least some of the protruding elements or pins 102 from surface of ring 100 to provide a snap connector. A latching mechanism or other connector can be used to secure the coupling elements together. These features are illustrated in one or more of the figures described herein.

Note that ring element 124 can be elevated above the surface of ring 122 by one or more millimeters. Peripheral wall 121 can thus have a height of at least 1 mm. This can provide for the insertion of lymphatic channels 106 to be a depth of at least 1 mm into the vein 128, for example. Thus, the relative dimensions of the coupling elements can define a depth of insertion.

Figure 2A:
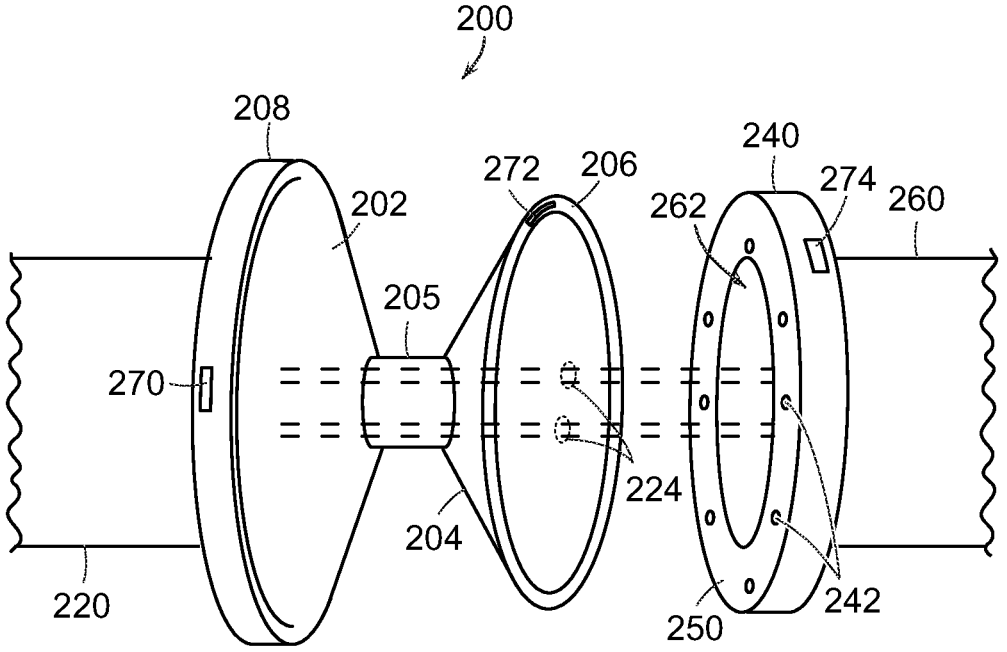
FIG. 2A illustrates an embodiment including a connector element to attach a pair of rings together that couple one or more lymphatic channels to a vein.
Figure 2B:
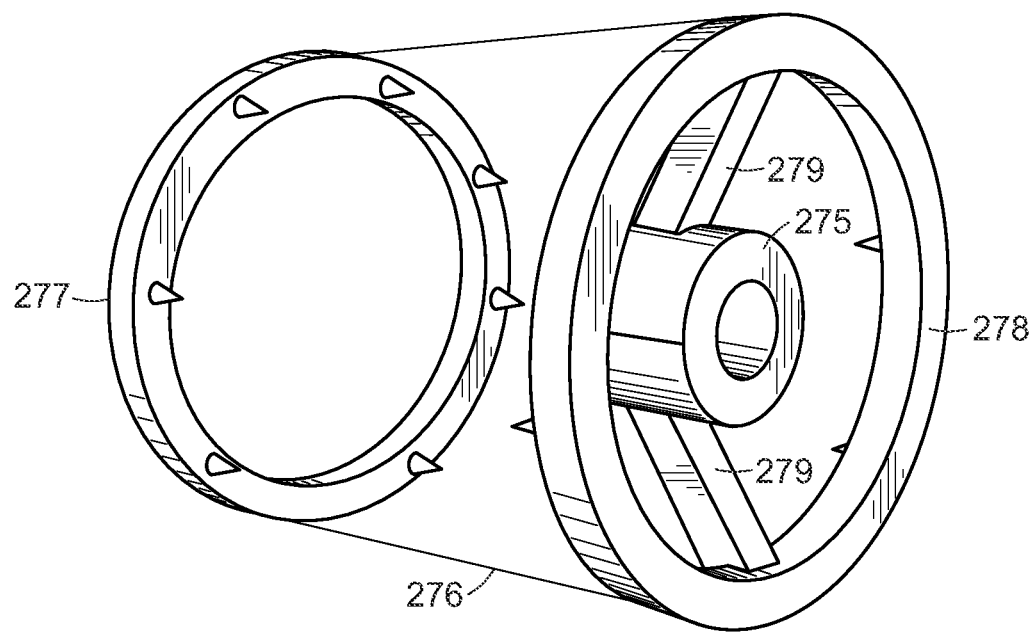
FIG. 2B illustrates a further embodiment including a central tube connected to a ring and an external sheath can be attached to enclose the coupling elements.

Shown in FIG. 2A is a coupler 200 having a first ring 208 that receives and anchors the vein 220 as described previously, however this mates to a first cone 202 shaped element having an open end that gradually narrows in diameter to a first end to an opening of a small diameter tube 205 where the lymphatic channels 224 are received from second cone 204 that narrows to the second end of tube 205. The wide end of cone 206 is sized and shaped to attach to an inward facing surface of first ring 240, that has pins, prongs or tissue anchors 242 that engage and secure adipose tissue with the lymphatic vessels 224 to the ring 240 wherein the tissue 260 surrounding the lymphatics is folded over the anchors 242 on surface 250, for example. The lymphatic vessels thus enter the open end of cone 206 and pass through a narrow opening into the tube 205 and into the vein. Note that the embodiment of FIG. 1 can employ a single cone that guides entry of the lymphatic vessels from the open end of the cone through a narrow opening of the cone and into the vein to define the junction at which lymph fluid enters the vein. Returning to FIG. 2A, the second ring 208 can include a first fluoroscopic marker 270, the cone 206 can include a second fluoroscopic marker 272, and second ring 240 can include a third fluoroscopic marker 274, for example, to illustrate the use of markers on the various embodiments described herein. Shown in FIG. 2B is a further embodiment in which first ring 277 can be connected to a second ring 278. Tube 275 is connected to ring 278 by a plurality of arms or connecting elements 279. The tube 275 has an internal cavity in which the vein can be inserted and attached to the tube as described herein. In preferred embodiments, the first and second rings can align upon a common axis when they are connected together. The pins or anchors can be arranged symmetrically about the common longitudinal axis. The pins or anchors for the vein can project in a first direction parallel to the common axis, whereas the pins or anchors for the connective supporting tissue can extend parallel to the common axis but in a second opposite direction.

Figure 2C:
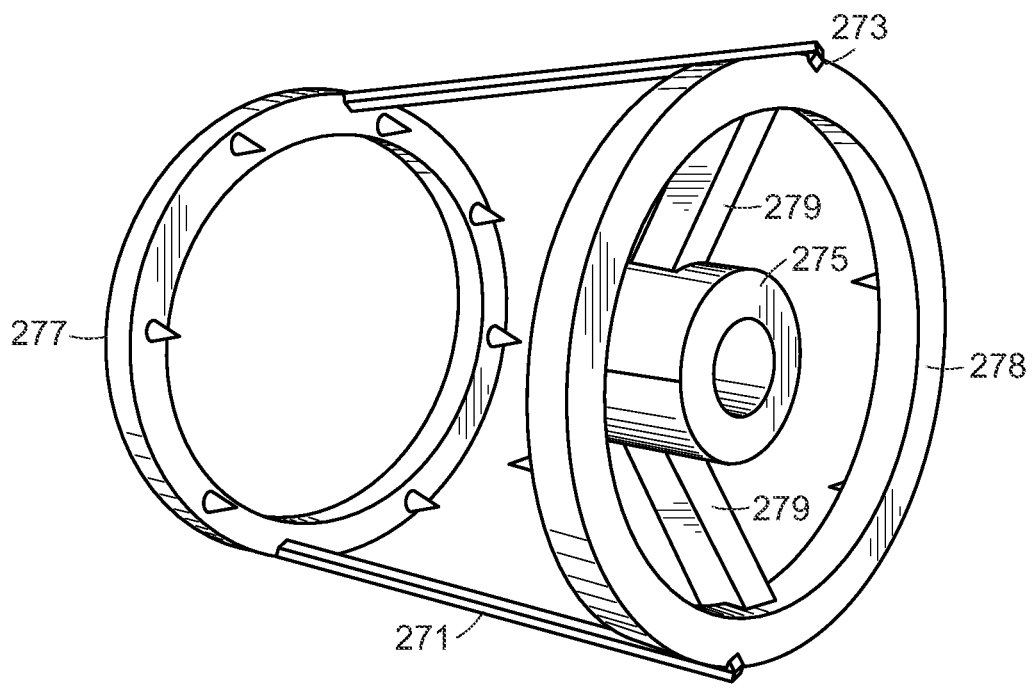
FIG. 2C illustrates a further mechanism for connecting a first coupling element to a second coupling element.

The embodiments described herein can be encapsulated within an outer sheath 276 extending around the rings that are aligned along a common axis upon being connected together. The first coupling element or ring can be connected to the second coupling element with one or more connector elements. As described herein, connector elements such as pins, posts or prongs can be used. As shown in FIG. 2C, a plurality of prongs 271, 273 can extend from the first ring to the second ring where inwardly facing protrusions or ridges grasp the outer edge of the second ring. The outer sheath or surfaces of the devices provide a smooth outer surface. Certain elements of the device can be flexible so as to move with the surrounding tissue of the patient. One or more elements of the device can comprise bioabsorbable materials. Selected surfaces may be porous so as to accommodate ingrowth and adhesion to tissue adjacent the device to stabilize the device within the tissue matrix. The length of the tube 275 (or tube 205) can be used to indicate to the user that the length of the lymphatic channels that extend into the vein are sufficiently long to prevent the lymphatic channel from becoming dislodged from the anastomosis. There is a junction region, preferably within the device housing, where the lymphatic vessels deliver lymph fluid into the vein. Note that the first and second coupling elements can optionally be connected on one side so that the user can simply rotate the two components relative to each other around a pivot axis to align and connect the elements while the channels are inserted into the vein. In a further embodiment an outer sheath 276 can be attached to the device that extends around the circumference of the device and thereby enclose the device. The sheath 276 can also comprise portions extending peripherally from each ring that connect together by a sheath connector.

Figures 2D, 2E:
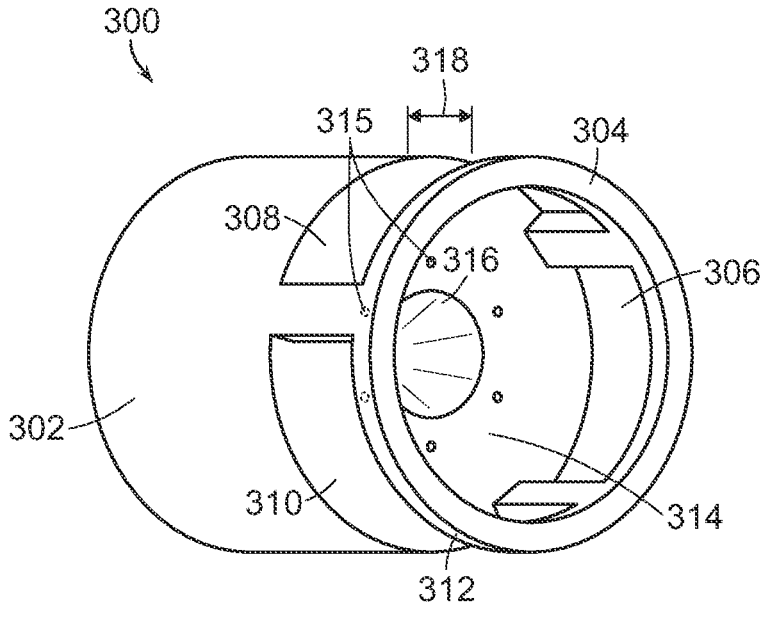
FIG. 2D illustrates perspective view of a first end of an implant for a lymphovenous bypass procedure.
FIG. 2E illustrates a further perspective view of a second end of the implant shown in FIG. 2D.

In a further embodiment, the coupling device can be fabricated as a single unitary piece that has a tubular portion to receive the vein though a first end such that the wall of the vein can be grasped by pins or anchors on a second end of the tubular portion. The second end of the device can have a larger opening that receives the supporting tissue containing the lymphatic vessels that are inserted into the vein. As shown in front view in FIG. 2D and in rear view in FIG. 2E, a coupling device 300 according to some embodiments described herein can have a body formed of a single, unitary piece, which can be fabricated using standard molding techniques, or by using three dimensional (3D) printing methods. In this embodiment, the coupling device 300 is defined by a cylindrical wall 302 that at least partially surrounds different portions of the coupling device 300. The cylindrical wall 302 can have sidewall openings 306, 308, 310 adjacent to an outer ring sidewall 312 in some embodiments. The sidewall openings 306, 308, 310 are sized to allow a user to pass a forceps or other tool first through one of the sidewall openings and then through the ring opening and past a bottom ring surface 304. The forceps can be used to grasp a tissue (such as adipose tissue surrounding lymphatic channels) and pull it through the ring opening and onto tissue grasping elements 324, such as pins anchors, at each opening 306, 308, 310. The pins may be inserted into pin securing areas or may be integrally formed with the coupling device 300, for example. In some embodiments, the coupling device 300 can have a center aperture 316 that extends from an inner bottom surface 314 to a top surface 320 of the coupling element 300. A vein can extend through the center aperture 316 from the top surface 320 and attached to tissue grasping elements 315 such as pins that may be inserted into pin securing areas or may be integrally formed with the coupling device 300. The tissue grasping elements 315 can protrude from the inner bottom surface 314, which is set at a depth 318 below the ring element. In some embodiments, the adipose tissue can be stretched onto the pins 324, which may cause extension of lymphatic vessels within the adipose tissue so that they will preferably extend into the vein secured at pins 315. The bottom ring surface opening has a larger size or diameter than the center aperture 316 as it must accommodate insertion of a larger volume of supporting tissue that contains the lymphatic channels to be fluidly coupled to the vein.

At the top surface 320, the surface around the center aperture 316 can be a cone-shaped surface 322. The cone-shaped surface 322 can help direct insertion of tissue by guiding the tissue into the center aperture 316 as force is applied to the tissue. In addition, the cone-shaped surface 322 can reduce abrasion on tissue (e.g., vein) that has been inserted as it does not have sharp corners or edges.

Figure 3:
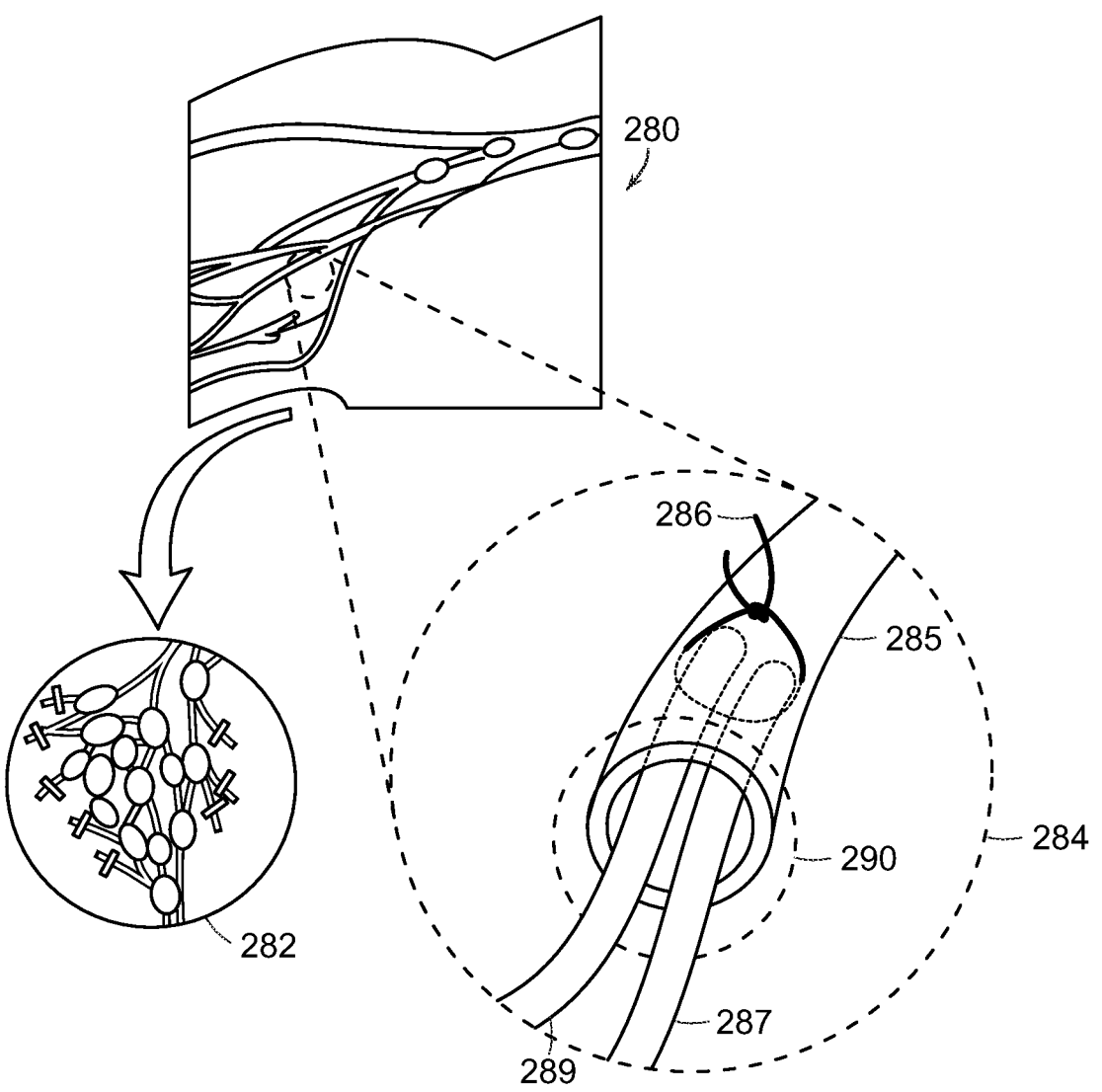
FIG. 3 illustrates an axillary anatomic region after dissection of level 1 and 2 lymph nodes where lymphatic channels glow from an FITC injection, described hereinafter and the bypass procedure has been performed.

FIG. 3 shows an enlarged view 284 of the axillary location 280 that includes lymph nodes 282 and a vein 285, that has received a pair of lymphatic vessels 287, 289. Unlike prior procedures which used a suture 286 to secure the channels to the vein 285, the present invention uses a coupler 290 at the junction of the channels 287, 289 entering the vein.

Shown schematically in FIG. 4 is a method 400 of performing a surgical procedure wherein, for example, a surgeon can perform an incision through the skin to access 402 tissue that includes one or more lymphatic channels. A coupling device is positioned into the patient 404 where a first coupling element is attached 406 to one or more lymphatic channels and a second coupling element is attached 408 to a vein. The first coupling element is connected 410 to a second coupling element such that the one or more lymphatic channels are positioned in the exposed vein opening to a depth such that lymph from the lymphatic channels can flow into the vein. The surgeon then closes 412 the surgical opening such that the coupling device is implanted in the patient. Alternatively, the coupling device can comprise a single tube or ring having pins or tissue anchors on one end to connect to a vein inserted into one open end of the tube. The wall tissue of the vein is placed onto the pins or tissue anchor elements which penetrate the wall tissue to hold the vein in place relative to the device. The lymphatic channels can be inserted through the tube opening at the opposite end and into the vein positioned at least partially within the tube. The tube may have internal features that permit insertion in one end but inhibit removal of the vein. Thus, an inner wall of the tube can have a frictional surface with teeth, pins, or other features directed in one direction to inhibit movement of the vein in the tube. The tube can have external features allowing a loop of material grasping the channels to be attached to the tube.

Dyes can be used to aid in visualization and mapping of the lymphatic system. Fluorescein isothiocyanate (FITC), for example, is excited in the visible spectrum and routinely used in the operating room. Neurosurgeons inject this dye intravenously and utilize microscopes equipped with filter technology to visualize tumors while maintaining life-like color of the surrounding tissues allowing for simultaneous magnification and tissue dissection. This is important for the lymphatic surgeon. Thus FITC can be used in the operating room for lymphatic mapping. Note, further that FITC has been utilized to perform a lymphovenous bypass (LVB) in the superficial tissues of the arm in a patient with chronic lymphedema. FITC is a safe and highly effective dye for lymphatic mapping and dissection in open surgical fields such as in the LYMPHA procedure.

Lymphedema repository data on all breast cancer patients that underwent the LYMPHA procedure included demographic information (age, body mass index [BMI]) and peri-operative data have been obtained (number of lymphatic channels visualized and bypassed, distance of channels from axillary vein, name of targeted vein, and adverse events).

In an exemplary procedure (see Spiguel et al. "Fluorescein Isothiocynate: A Novel Application for Lymphatic Surgery", Annals of Plastic Surgery, Volume 78 (2017), the entire contents of which is incorporated herein by reference), prior to the ALND, 2 cc of a modified 2% fluorescein solution are injected intradermally and along the muscle fascia of the ipsilateral upper arm, for example. The solution can be modified from the stock AK-FLUOR 10% (Akorn Inc., Lake Forest, IL) solution by diluting 2 cc with 7.5 cc of normal saline and 0.5 cc of AlbuRx5 (CSL Behring Inc., King of Prussia, PA). The ALND is performed with attention to preserving a superficial accessory vein tributary which longitudinally traverses the level I lymph nodes. The superior dissection of the level I axillary contents along the axillary vein is performed with identification of the accessory vein tributary which is typically found anterior to the thoracodorsal neurovascular bundle. The vein is then dissected free from the level I axillary contents and clipped distally to provide maximal length. Completion of the level I and II ALND is then performed.

Following completion of the axillary dissection, for example, a Pentero 900D Microscope (Carl Zeiss Inc., Germany) equipped with the YELLOW 560 package, can be utilized to identify and map the divided lymphatic channels draining the arm. The harvested vein is prepared per standard microsurgical techniques. Utilizing existing techniques, a surgeon, using 9-0 nylon suture, places a "U" stitch to capture the anterior wall of the vein and parachute in the lymphatic channels chosen for bypass. 10-0 nylon can then be utilized to suture the wall of the vein to the perilymphatic tissue. Channels not bypassed are clipped. Lymphatic flow filling the vein can be visualized with the filter activated one hour after anastomosis.

However, in accordance with selected embodiments, the surgeon, instead of suturing, will attached the perilymphatic tissue to a first connecting element and attach the vein to a second connecting element, insert the exposed ends of the lymphatic channels into the opening at the vein and connect these components to securely complete the anastomosis or intussusception of lymphatic channels into the vein.

As noted in the study by Spiguel, et al, thirteen patients underwent LYMPHA with intra-operative FITC lymphatic imaging from March to September 2015. Average patient age was 50 years with a mean BMI of 28. On average, 3.4 divided lymphatic channels (range 1-8) were identified at an average distance of 2.72 cm (range 0.25-5 cm) caudal to the axillary vein. 1.7 channels were bypassed per patient (0-4). Anastomoses were performed to the accessory branch of the axillary vein and or to a lateral branch. LYMPHA added an average of 67 minutes (45-120 minutes) to the oncologic procedure in these examples.

Thus, FITC is a safe and effective dye for the LYMPHA technique. In comparison to ICG and blue dye, FITC has many advantages. FITC does not permanently stain surrounding tissues, as opposed to ICG and blue dyes, which facilitates dissection of the lymphatic channels. The primary advantage of FITC over ICG in lymphatic surgery, for example, is the ability to allow for simultaneous visualization and dissection of lymphatic channels as FITC is excited in the visible spectrum making it a dye to be used in open surgical fields.

Diagnosed breast cancer patients can have a lymphedema evaluation pre-operatively. Each evaluation, pre-operatively and post-operatively, can include three components: (1) evaluation by a certified lymphedema therapist for signs and symptoms of BCRL, (2) circumferential measurements, and (3) bioimpedance spectroscopy. Lymphedema can be defined as having signs/symptoms of BCRL and one positive objective measure and can be transient or extend beyond 6 months, for example. Demographics (age, BMI, prior radiation or chemotherapy), cancer treatment characteristics (chemotherapy, type of radiation treatment, and surgical management), and physical therapy evaluations (circumferential measurements, bioimpedance spectroscopy data, follow-up) can be included in the analysis.

An ALND procedure includes resection of axillary level I and II nodes. Patients undergoing an ALND can undergo identification of divided lymphatics with FITC and subsequently re-route those channels into a preserved axillary vein tributary.

Demographics and potential risk factors for development of lymphedema such as age, body mass index, clinical stage, radiotherapy, and chemotherapy were reviewed. Similarly, patients who underwent the LYMPHA technique were compared to those who only had ALND.

All p-values were computed using the Fisher Exact Test or two-tailed t-test, as appropriate. Computations were done in the R language for statistical computing, version 3.3.2. A power analysis can be performed using SAS with the Fischer's Exact Conditional Test, for example. This utilized a set control percentage of 0.40 based on our institutional data. As previously noted, the incidence of lymphedema after simultaneous lymphovenous bypass was 0.04. Conservatively, in evaluating this procedure the power can be set at 0.8.

In a study conducted by Hahamoff et al ("A Lymphatic Surveillance Program for Breast Cancer Patients Reveals the Promise of Surgical Prevention", Journal of Surgical Research, 2017, 10.008, the entire contents of which is incorporated here by reference) 177 patients presented for a pre-operative lymphedema evaluation and 87 patients (49%) participated in the program over the period. 45% (67/145) of patients undergoing sentinel lymph node (SLN) biopsy and 64% (18/28) of patients undergoing ALND participated in the program and had an average age of 60 (range 32-83) and BMI 30 (range 17-46). 40% underwent a mastectomy and 21% underwent an ALND. 18% received neoadjuvant chemotherapy and 24% received RLNR. Most patients in this example did not undergo any reconstruction (62%).

The single most significant risk factor for the development of lymphedema was an ALND (p<0.001). Undergoing mastectomy (p=0.02), adjuvant chemotherapy (p=0.03), and RLNR (p=0.05) were also associated with lymphedema development. A trend towards lymphedema development and clinical stage III disease (p=0.10) was also noted.

TABLE 1

Advantages and disadvantages of the two most
commonly used fluorophores in lymphatic surgery
(Blue Dye and ICG) in comparison to FITC.

| Dye | Advantages | Disadvantages |
|---|---|---|
| Blue Dye | Technical<br>✓Visualized through Binoculars (Live Surgery)<br>✓No Specialized Equipment Necessary | Technical<br>XNo Depth of Penetration<br>XPermanent Staining<br>Safety<br>XAdverse Reactions<br>Skin Necrosis (Methylene Blue)<br>Anaphylaxis (Isosulfan Blue)<br>XCross Reactivity |

TABLE 1-continued

Advantages and disadvantages of the two most
commonly used fluorophores in lymphatic surgery
(Blue Dye and ICG) in comparison to FITC.

| Dye | Advantages | Disadvantages |
|---|---|---|
| ICG | Technical<br>✓Depth of penetration = 20 mm<br>Safety<br>✓No adverse reactions (dermal)<br>✓No cross-reactivities | Sulfa Drugs (Isosulfan Blue)<br>SSRI (Methylene Blue)<br>Technical<br>XUnable to visualize through binoculars (No Live Surgery)<br>XPermanent staining<br>X(Requires Specialized Equipment |
| FITC | Technical<br>✓Visualized Through Binoculars (Live Surgery)<br>✓Depth of penetration = 5 mm<br>✓No permanent staining<br>Safety<br>✓No adverse reactions (dermal)<br>✓No cross reactivities | Technical<br>XRequires Specialized Equipment |

All patients who developed lymphedema were initially diagnosed either during treatment or within six months of the completion of their cancer therapy. Therefore, all patients were initially diagnosed with transient lymphedema. The average time to diagnosis after the surgical procedure was 4.7 months. One patient in the SLN biopsy group developed transient and then persistent lymphedema (1/67 or 1.5%). Of five patients who developed transient lymphedema after undergoing an ALND without the LYMPHA procedure, one patient's symptoms and objective measures completely resolved and four patients' symptoms persisted and they developed lymphedema (4/10 or 40%). Of these four patients, three were diagnosed with lymphedema based on changes in symptoms with associated changes in circumferential measurements and bioimpedance spectroscopy. The fourth patient was diagnosed based on symptoms and changes in circumferential measurements alone. Of the 17 patients who underwent the LYMPHA procedure during the period, only eight participated in our surveillance program. One patient in the ALND+LYMPHA group developed transient lymphedema which was persistent but still within six months of the completion of adjuvant radiation therapy (⅛ or 12.5%). This patient's diagnosis was based on changes in symptoms and bioimpedance without change in circumferential measurements. The only significant difference between the two groups undergoing ALND with or without LYMPHA was the follow-up period of 15 months versus 20 months (p<0.03), respectively.

In a comparison of patients who underwent ALND with or without LYMPHA versus those lost to follow-up in order to identify any potential confounding factors or bias, the only difference between groups noted is that participants who underwent LYMPHA were 10 years older than those patients lost to follow-up (59 vs 49, p=0.04).

With no cure to date for BCRL, recognition and prophylactic treatment for high-risk patients is an important consideration. The rate of lymphedema after ALND can be reduced from 40% to 12.5% after introduction of the LYMPHA approach in this example. Similarly, it is preferable to identify lymphedema in patients undergoing ALND within five months of their procedure. ALND, mastectomy, adjuvant chemotherapy, and RLNR were associated with the development of lymphedema.

A notable finding of the Hahamoff et al, study was the reduction in rate of lymphedema development from 40% to 12.5% in patients undergoing an ALND after the introduction of the LYMPHA technique.

Note that the patients who develop lymphedema presented initially with signs and symptoms either during treatment or within six months of the end of their cancer therapy. Of these patients, one patient's condition completely resolved. No patient, to date, has presented with lymphedema more than six months after the completion of cancer therapy. This finding underscores the value of surveillance in being able to detect early lymphedema which is especially important for high-risk patients as prompt detection and treatment can potentially slow the progression of disease.

ALND and RLNR are important risk factors for the development of lymphedema. There can be increased rate of lymphedema in patients undergoing mastectomy, and this can be explained by the indications for ALND. Specifically, patients with limited nodal involvement undergoing lumpectomy do not require an ALND while those undergoing mastectomy will undergo an ALND for the same extent of nodal involvement. Therefore, patients undergoing mastectomy receive more aggressive axillary management than those undergoing lumpectomy. There can be increased rates of lymphedema for patients who underwent adjuvant chemotherapy, which again, may be biased as those undergoing chemotherapy are more likely to have presented with more advanced disease initially. However, studies have linked specific chemotherapy regimens to the development of lymphedema. Lastly, as patients presenting for ALND have more advanced disease, it is not surprising that increased rates of lymphedema development were noted in those with clinical stage 3 disease.

While surgical prevention can aid in improving the quality of life in breast cancer survivors, development of this program did have challenges. When SLNs were sent for permanent section and the patient returned to the operating room for an ALND at a later date, scheduling combination procedures between a breast and plastic surgeon were effective. However, when SLNs were sent for frozen section, the scheduling can be more erratic as a larger percentage of patients will never progress to ALND especially in light of recent trials challenging the need for ALND.

The present devices and methods for the treatment of lymphedema can change how metastatic disease to the axilla is treated. Given the significant morbidity of ALND, namely lymphedema, there is a distinct push away from ALND in early stage breast cancer in place of RLNR. However, with improved LYMPHA procedures and the promise of lower rates of lymphedema, the role of ALND in providing an improved method of loco-regional control can be enhanced.

A significant finding was that a decrease in lymphedema rates after the advent of LYMPHA are notable as the average time to diagnosis of lymphedema was 4.7 months following the surgical intervention. In this example, the total follow-up time in the ALND versus ALND+LYMPHA groups was 20 months and 15 months, respectively.

Offering LYMPHA with ALND together decreased the rate of lymphedema from 40% to 12.5%. Similarly, surveillance after surgery can provide early diagnosis and intervention by physical therapy. The significant risk factors for lymphedema development included ALND, RLNR, adjuvant chemotherapy, and mastectomy.

Figure 5:
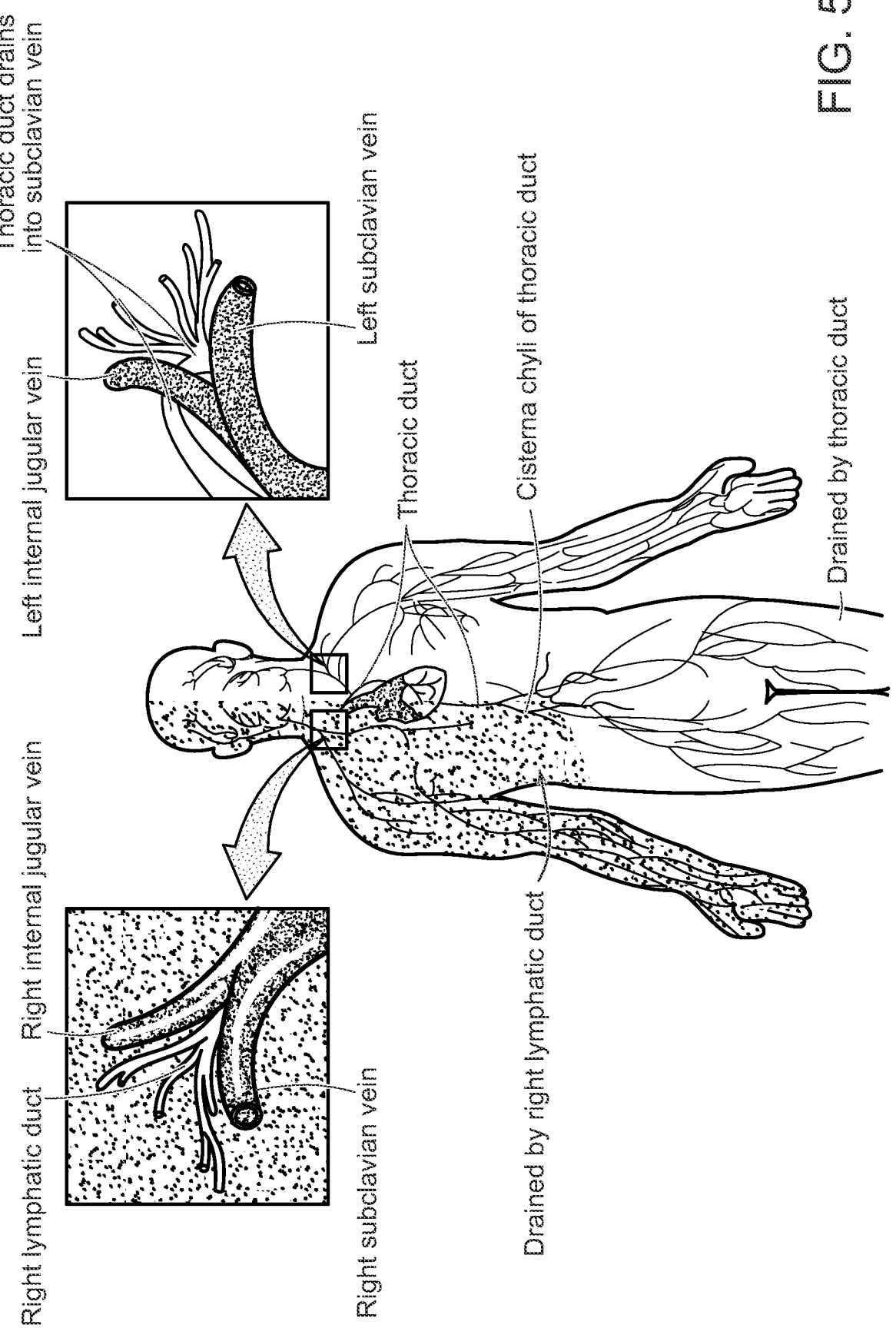
FIG. 5 schematically illustrates the lymphatic channel system of the human body wherein a bypass procedure in accordance with the invention can be performed at different locations to reduce lymphedema.

Note that breast surgeons often prefer to use a dual tracer method including both blue dye and technetium sulfur colloid for sentinel lymph node (SLN) identification. This is especially important in cases where neoadjuvant chemotherapy has previously been administered. Therefore, a different dye was sought for arm lymphatic mapping to differentiate staining from arm versus breast lymphatics. Thus, a combination of visualization procedures can be used. Shown in FIG. 5 are regions of the body containing portions of the lymphatic system. Each of these regions can be imaged to map the flow of lymph as needed for a particular condition.

The most common method of lymphatic vessel mapping currently in use is indocyanine green (ICG). However, the challenge with ICG is that the dye is near-infrared and therefore excited in the non-visible spectrum. This limits the usefulness of ICG for visualization and simultaneous dissection as the dye is displayed as a white signal on a black background and cannot be concurrently visualized through the binoculars of a microscope.

Figure 6:
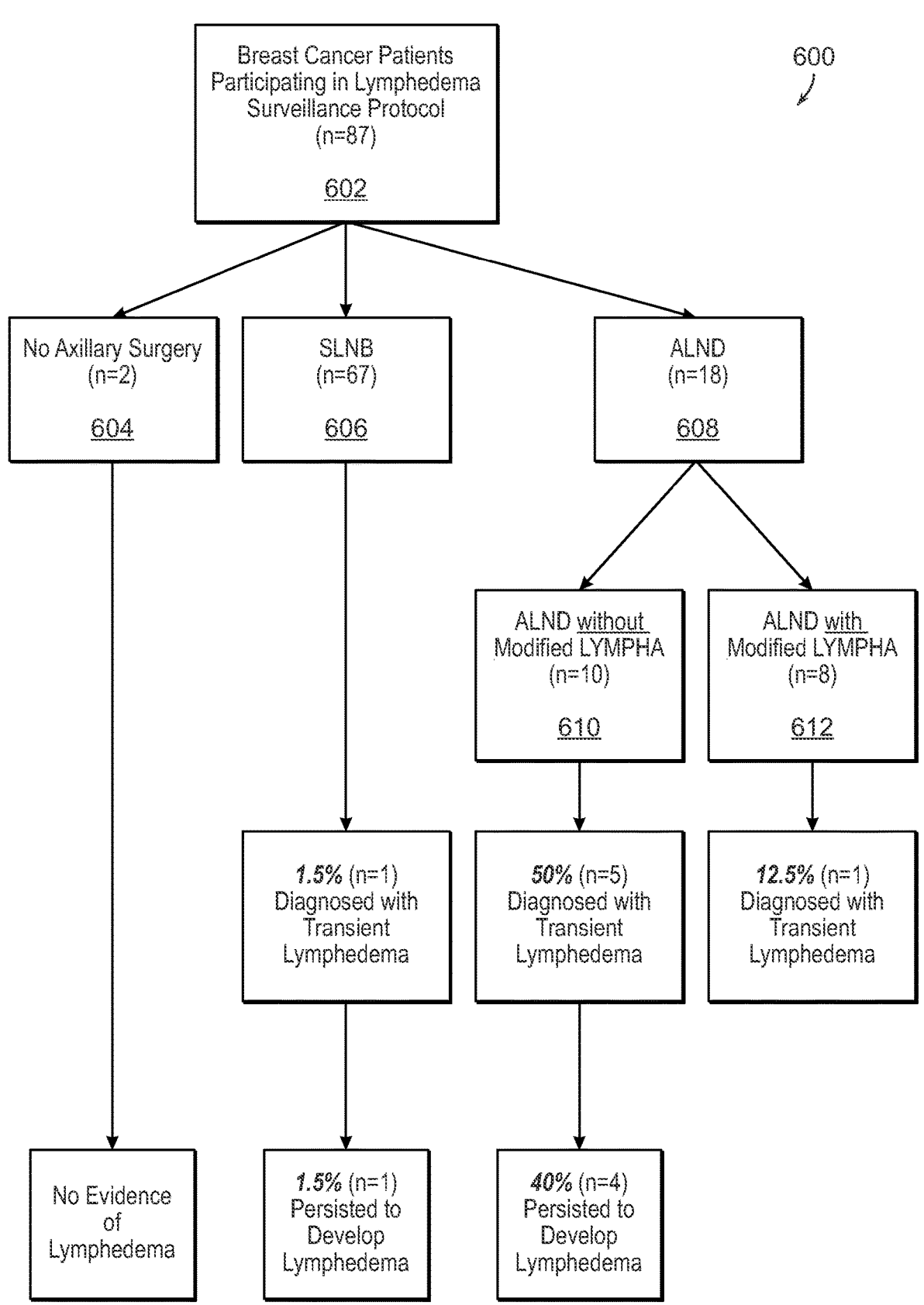
FIG. 6 illustrates a flowchart of lymphedema protocols used in conjunction with surgical procedures described herein.

Illustrated in FIG. 6 is a flowchart 600 exhibiting the steps associated with treating lymphedema in cancer patients. The process is initiated at 602 where patients can be routed through one of three distinct protocols 604, 606, 608. In the first protocol 604, no axillary surgery is performed and follow up indicates that there is no observed lymphedema. The second protocol 606 employs sentinel lymph node biopsy where a certain population develops lymphedema requiring treatment. A third protocol 608 involved performing an ALND procedure either with 612, or without 610, a LYMPHA procedure as described herein.

Figure 7:
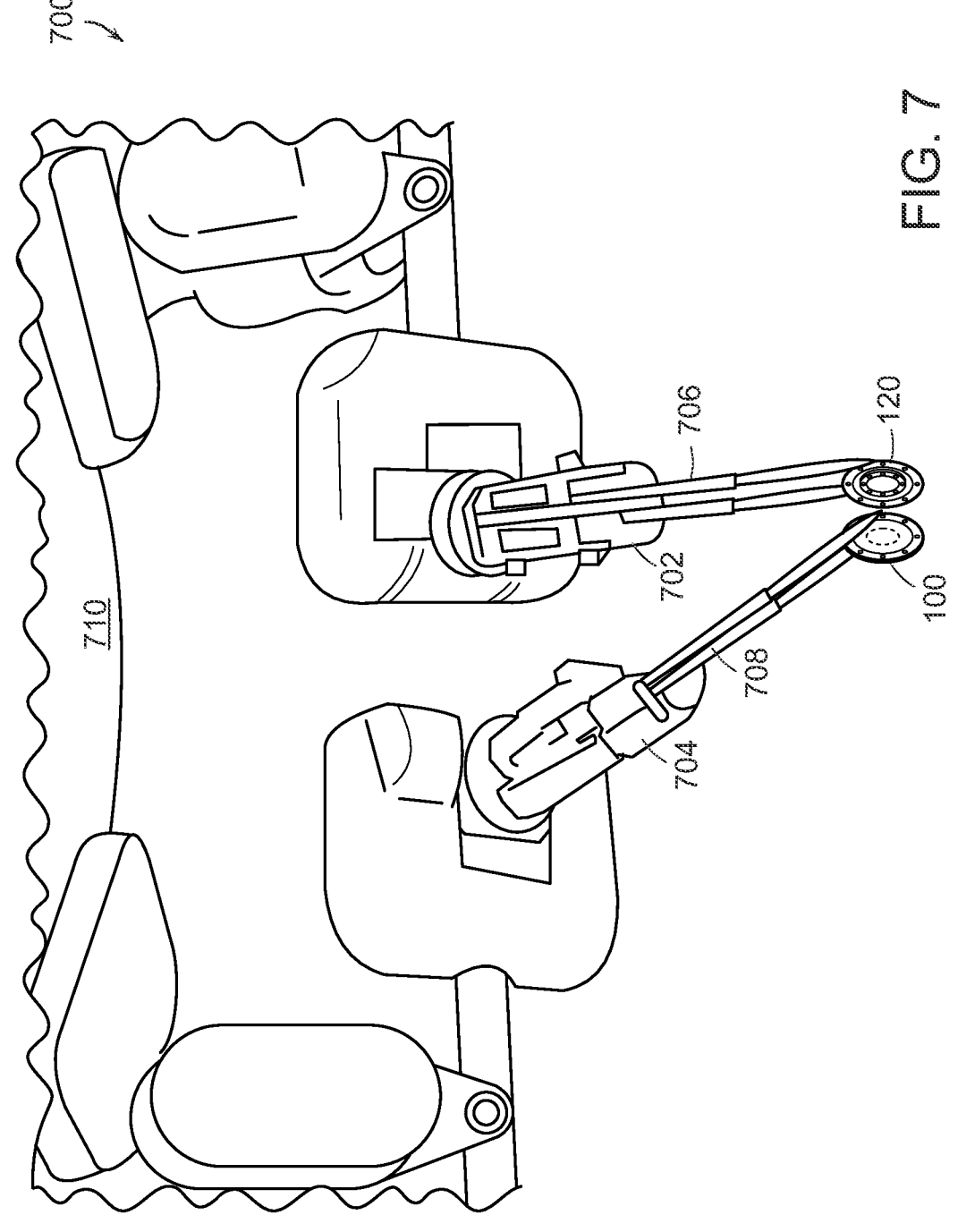
FIG. 7 illustrates a robotic control system having computerized control of arms with manipulators such that a surgeon can perform procedures in accordance with preferred embodiments hereof.

Illustrated in connection with FIGS. 7 and 8 are systems and methods for performing a robotic lymphovenous bypass surgical procedure for implanting a coupling device as described herein. Robotic systems such as the Da Vinci system available from Intuitive Surgical Inc., Sunnyvale CA, have been used to perform the LVA microsurgical procedure as illustrated in connection with FIG. 3. See van Mulken et al, "First-in-human robotic supermicrosurgery using a dedicated microsurgical robot for treating breast cancer-related lymphedema: a randomized pilot trial", Nature Communications, 11:757, Feb. 20, 2020, the entire contents of which is incorporated herein by reference. Further details concerning robotic surgery are described in U.S. Pat. No. 9,138,297, the entire contents of which is incorporated herein by reference. This system 700 can employ robotic arms 702, 704 attached to grasping elements 706, 708 such as forceps-like manipulators. A surgeon can use the system 700 to grasp and control microsurgical tools within the surgical field. The computerized system 710 in the system 700 is programmed with software to perform scaling motion and tremor filtration, for example. As described in the process flow diagram of FIG. 8, the process 800 uses a plurality of two or more control arms 702, 704 that are actuated to perform the procedure wherein a vein is selected 802 having a diameter suitable for coupling to a first (or second) coupling element as described herein. The robotic arms can further grasp a region of adipose tissue having one or more lymphatic vessels wherein the adipose tissue is attached 804 to the second (or first) coupling element as described herein. The robotic arms can grasp the first and second coupling elements 100, 120, as seen in FIG. 7, to align the two elements such that the lymphatic vessels are inserted into the vein 806, typically under surgical microscope visualization. The robotic grasping tools 706, 708 can hold the two coupling elements by the outer peripheral surfaces which may be made with notches or slots to enable a stable and secure grip. The two coupling elements are connected 808 to each other and the device is positioned within the wound opening for closing 810 of the wound.

Figure 9:
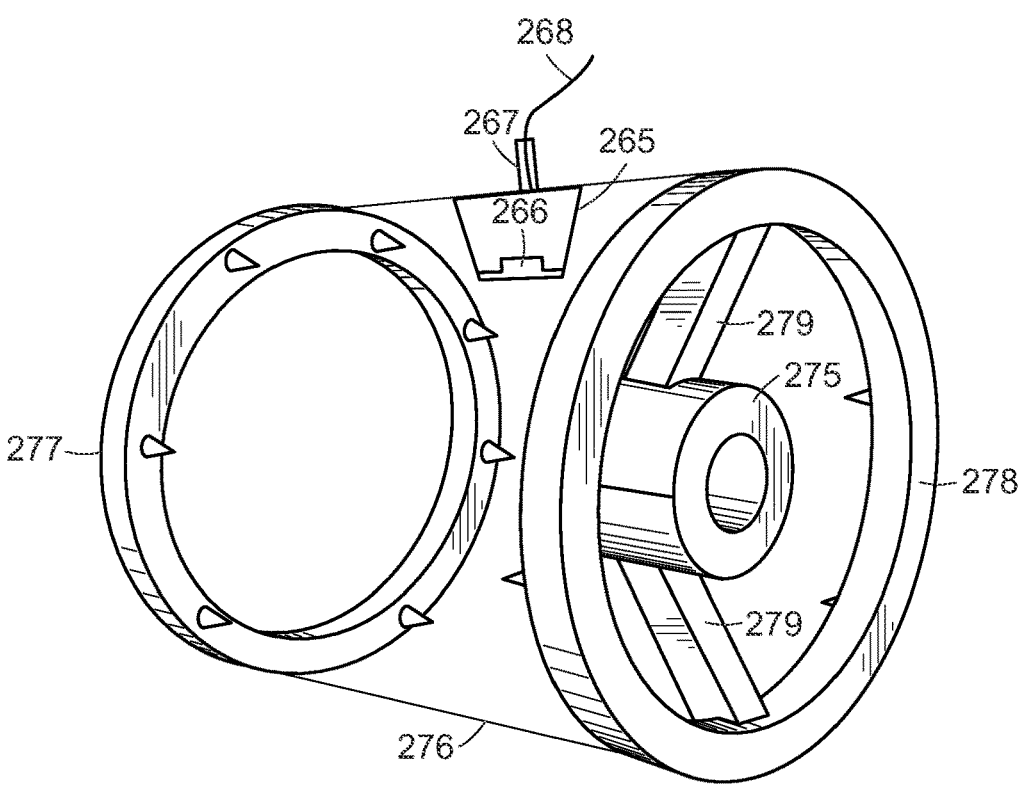
FIG. 9 illustrates a sensor mounted to a connector device for measuring flow of lymph fluid into the vein.
Figure 10:
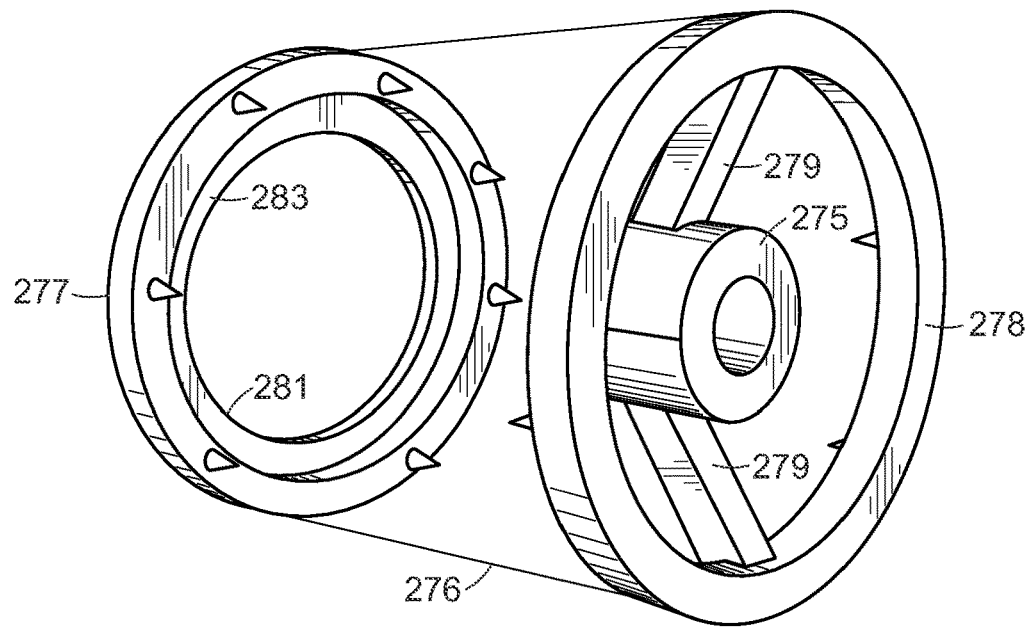
FIG. 10 illustrates a valve device for controlling fluid pressure at a junction in the vein at which lymph fluid enters into the vein.

As shown in FIG. 9, one or more sensors 265 or imaging devices can be used to measure the flow of lymph fluid into the vein at the junction within the device. The sensor 265 can be an optical sensor, for example, wherein a light source such as a light emitting diode (LED) or laser diode can be positioned relative to a photodetector array within a sensor module 266 that contacts the outer surface of the vein. As described herein, a fluorescent dye can be delivered into the lymphatic vessels prior to, during or after the procedure such that the optical sensor can measure the flow rate by detecting movement of the dye. Alternatively, the sensor 265 can comprise an ultrasound transducer 266 that can transmit an acoustic signal into the vein to detect reflectors that are introduced into the lymphatic vessels with the fluorescent dye. A cable or wire 268 can extend through a transcutaneous port 267 that extends to the tissue surface after wound closure. The cable is connected to a computer controlled data processing and display device for viewing of the measured data on the display and for storage of the data in a memory. This data can be transported to the electronic medical record for each patient. The sensor can be sized and configured to be inserted through the port in certain embodiments so as to enable easy insertion and removal after wound closure. As described previously, the sensor and/or fluoroscopic imaging can optionally be used during and/or after the procedure to verify proper positioning of the lymphatic vessels and lymph flow. The device can optionally also be coated with one or more therapeutic agents that inhibit clot formation within the vein in proximity to the junction. Shown in FIG. 10 is a further embodiment in which a flexible valve ring 281 can be attached to the coupling element 277 with a membrane 283. The inner surface of valve element 281 is in contact with the outer surface of the vein that is attached to the pins shown on inner surface of element 277. The valve element can be sized to constrict the vein so as to limit venous pressure on the junction within device so as to decrease backpressure from the vein fluid on the junction region. This reduced pressure at the junction can aid in establishing flow of lymph fluid which tends to increase over time. The valve element can be shaped, sized and configured to accommodate the slow increase in lymph fluid pressure at the junction and can reduce the amount of compression over time. The valve element can comprise a biodegradable material that eases the constraint on the vein overtime due to the rate of degradation of the material. The valve can also be active, such as by a pressurized bladder that can release a pressurized fluid such as saline over time. Alternatively, pliable flaps can also impart sufficient pressure on the vein with an elastic material that expands at a selected rate.

It will be appreciated by those skilled in the art that modifications to, and variations of the above described device and methods can be made without departing from the inventive concepts disclosed herein. Accordingly, the disclosure should not be viewed as limited except as by the scope and spirit of the appended claims.

The invention claimed is:

1. A method of performing a lymphovenous bypass surgical procedure comprising:

positioning a unitary body coupling device relative to a surgical opening of a patient, the unitary body coupling device having a central aperture, and a tubular body extending between a first end and a second end;

attaching the first end of the unitary body coupling device to a vein of the patient and the second end to adipose tissue that supports a plurality of lymphatic channels of the patient, the plurality of lymphatic channels being inserted through the central aperture of the unitary body coupling device wherein open ends of the plurality of lymphatic channels extend to a distance within an open end of the vein such that lymphatic fluid within at least one of the plurality of lymphatic channels flows into the vein; and implanting the unitary body coupling device into the patient.

2. The method of claim 1 wherein attaching the second end to the adipose tissue further comprises inserting pins on a ring of the unitary body coupling device into the adipose tissue.

3. The method of claim 1 wherein the plurality of lymphatic channels intussuscepts the vein by extending the distance into the vein.

4. The method of claim 1 further comprising coupling at least three of the plurality of lymphatic channels that are positioned within surrounding supporting adipose tissue to the second end.

5. The method of claim 1 further comprising imaging a region of a patient to generate image data and mapping the plurality of lymphatic channels in the region.

6. The method of claim 5 further comprising selecting one or more lymphatic channels of the mapped lymphatic channels for a bypass procedure from the mapped image data.

7. The method of claim 1 further comprising inserting the plurality of lymphatic channels to a depth of at least 1 mm inside the vein.

8. The method of claim 1 further comprising coupling at least 3 lymphatic channels into a single vein.

9. The method of claim 1 further comprising inserting at least one of the plurality of lymphatic channels into a sidewall of the vein.

10. The method of claim 1 further comprising measuring a flow of the lymph fluid into the vein or a vein tributary.

11. The method of claim 1 further comprising imaging a coupling of the plurality of lymphatic channels into the vein or a vein tributary.

12. The method of claim 1 further comprising connecting a second lymphatic channel to a second vein with a second lymphovenous bypass unitary body coupling device.

13. The method of claim 1 further comprising implanting the unitary body coupling device into an arm of a patient to treat lymphedema or into a leg of a patient.

14. The method of claim 1 further comprising robotically performing one or more steps of the method wherein a plurality of robotic arms holds a corresponding plurality of microsurgical tools that grasp at least one of the adipose tissue that includes the plurality of lymphatic channels and the vein to connect the lymphatic channels and the vein together with the unitary body coupling device.

15. The method of claim 1, further comprising extending the vein into the unitary body coupling device through the central aperture to a cone shaped surface on the unitary body coupling device that is aligned to receive the plurality of lymphatic channels.

16. A method of performing a lymphovenous bypass surgical procedure comprising:

positioning a tissue coupling device relative to a surgical opening of a patient, the tissue coupling device having a first plurality of tissue grasping elements and a second plurality of tissue grasping elements on a unitary tubular body having an aperture extending through the tubular body;

attaching the first plurality of tissue grasping elements to a vein of the patient;

attaching the second plurality of tissue grasping elements to adipose tissue that includes a plurality of lymphatic channels of a patient that extend through the aperture of the unitary tubular body such that open ends of the plurality of lymphatic channels are positioned at least a distance within an open end of the vein; and implanting the tissue coupling device into the patient such that lymphatic fluid flows from at least one of the plurality of lymphatic channels into the vein.

17. The method of claim 16 wherein attaching the first tissue grasping elements further comprises inserting pins on a ring of the tissue coupling device into the vein, the ring having an aperture to receive the vein.

18. The method of claim 16 wherein the plurality of lymphatic channels intussuscepts the vein by extending a distance of at least one millimeter into the vein.

19. The method of claim 16 further comprising imaging a region of a patient to generate image data, mapping the plurality of lymphatic channels in the region, and selecting one or more lymphatic channels of the mapped lymphatic channels for a bypass procedure from the mapped image data.

20. The method of claim 16 further comprising coupling at least 3 lymphatic channels into a single vein.

21. The method of claim 16 further comprising inserting one or more of the plurality of lymphatic channels to a selected depth in a single vein.

22. The method of claim 16 further comprising measuring a flow of the lymph fluid into the vein or a vein tributary.

23. The method of claim 16 further comprising imaging the coupling of the plurality of lymphatic channels into the vein or a vein tributary.

24. The method of claim 16 further comprising connecting a second lymphatic channel to a second vein with a second tissue coupling device.

25. The method of claim 16 wherein the tissue coupling device is implanted into an arm of a patient to treat lymphedema or is implanted into a leg of a patient.

26. The method of claim 16, further comprising extending the vein into the unitary tubular body having a cone shaped surface wherein the open end of the vein receives the plurality of lymphatic channels.

\* \* \* \* \*